(12) United States Patent
Dobrovolny (10) Patent No.: US 7,156,806 B2
(45) Date of Patent: Jan. 2, 2007

(54) STABILIZED TABLE RAIL CLAMP

(75) Inventor: Walter J. Dobrovolny, St. Paul, MN (US)

(73) Assignee: Minnesota Scientific, Inc., St. Paul, MN (US)

(*) Notice: Subject to any disclaimer, the term of this patent is extended or adjusted under 35 U.S.C. 154(b) by 441 days.

(21) Appl. No.: 10/643,012

(22) Filed: Aug. 18, 2003

(65) Prior Publication Data

US 2004/0073091 A1     Apr. 15, 2004

Related U.S. Application Data

(60) Provisional application No. 60/405,630, filed on Aug. 23, 2002.

(51) Int. Cl.
*A61B 5/00* (2006.01)

(52) U.S. Cl. ............... 600/230; 403/323; 403/322.1

(58) Field of Classification Search ........... 403/321, 403/322.1, 322.4, 323, 373, 374.2, 374.3, 403/374.4, 374.5, 374.1; 5/507.4, 646, 647; 248/229.12, 228.3, 245, 201, 214, 227.2, 248/231.71, 276.1; 600/227–234, 102, 212, 600/215; 108/28; 378/209
See application file for complete search history.

(56) References Cited

U.S. PATENT DOCUMENTS

| | | |
|---|---|---|
| 1,198,186 A | 9/1916 | Brown |
| 1,747,799 A | 2/1930 | Straus |
| 2,586,488 A | 2/1952 | Smith ............ 128/20 |
| 2,594,086 A | 4/1952 | Smith ............ 128/20 |
| 3,040,736 A | 6/1962 | Grieshaber ............ 128/20 |
| 3,221,743 A | 12/1965 | Thompson et al. ......... 128/303 |
| 3,572,326 A * | 3/1971 | Jensen ............ 600/233 |
| 3,638,973 A | 2/1972 | Poletti ............ 285/184 |
| 3,710,783 A | 1/1973 | Jascalevich ............ 128/20 |
| 3,810,462 A | 5/1974 | Szpur ............ 128/20 |
| 3,823,709 A | 7/1974 | McGuire ............ 128/20 |
| 3,858,578 A | 1/1975 | Milo ............ 128/20 |
| 3,970,075 A | 7/1976 | Sindelar et al. ............ 128/20 |
| 4,010,741 A | 3/1977 | Gauthier ............ 128/20 |
| 4,018,412 A * | 4/1977 | Kees et al. ............ 248/214 |
| 4,143,652 A | 3/1979 | Meier et al. ............ 128/20 |
| 4,254,763 A * | 3/1981 | McCready et al. ......... 600/230 |
| 4,355,631 A * | 10/1982 | LeVahn ............ 600/230 |

(Continued)

FOREIGN PATENT DOCUMENTS

FR      446439      3/1949

(Continued)

OTHER PUBLICATIONS

King, Jr., Use of Table-Fixed Abdominal Retractors, *American Journal of Surgery*, vol. 108, pp. 606-609, Nov. 1964.

(Continued)

*Primary Examiner*—James R. Brittain
*Assistant Examiner*—Daniel J. Mills
(74) *Attorney, Agent, or Firm*—Westman, Champlin & Kelly, P.A.; Z. Peter Sawicki (57) ABSTRACT

A clamping device which secures a retractor support apparatus to an operating table having a side rail. The clamping device has a first clamping member disposed between a side of the operating table and the side rail. The clamping device also includes a second clamping member disposed between the side rail and the first clamping member. A first securing mechanism operably connects the first and second clamping members such that a force provided by the first securing mechanism causes the first and second clamping members to move in opposing directions and frictionally engage the side of the operating table and the side rail.

22 Claims, 6 Drawing Sheets

U.S. PATENT DOCUMENTS

| | | | |
|---|---|---|---|
| 4,421,108 A | 12/1983 | Cabrera et al. | 128/20 |
| 4,424,724 A | 1/1984 | Bookwalter et al. | 74/540 |
| 4,461,284 A | 7/1984 | Fackler | 128/20 |
| 4,467,791 A | 8/1984 | Cabrera et al. | 128/20 |
| 4,491,435 A | 1/1985 | Meier | 403/55 |
| 4,573,452 A | 3/1986 | Greenberg | 128/20 |
| 4,617,916 A | 10/1986 | LeVahn et al. | 128/20 |
| 4,718,151 A | 1/1988 | LeVahn et al. | 24/535 |
| 4,805,599 A | 2/1989 | Ray | 128/2 |
| 4,813,401 A | 3/1989 | Grieshaber | 128/20 |
| 4,852,552 A | 8/1989 | Chaux | 128/20 |
| 4,949,707 A | 8/1990 | LeVahn et al. | 128/20 |
| 4,971,037 A * | 11/1990 | Pelta | 600/234 |
| 4,971,038 A | 11/1990 | Farley | 128/20 |
| 5,000,163 A * | 3/1991 | Ray et al. | 600/233 |
| 5,025,780 A | 6/1991 | Farley | 128/20 |
| 5,320,320 A | 6/1994 | Thompson | 248/316.1 |
| 5,380,338 A | 1/1995 | Christian | 606/130 |
| 5,400,772 A * | 3/1995 | LeVahn et al. | 600/230 |
| 5,556,067 A | 9/1996 | Konig et al. | 248/220.21 |
| 5,704,900 A * | 1/1998 | Dobrovolny et al. | 600/229 |
| 5,713,245 A * | 2/1998 | Bobbitt et al. | 74/493 |
| 5,722,935 A | 3/1998 | Christian | 600/214 |
| 5,741,210 A * | 4/1998 | Dobrovolny | 600/227 |
| 5,882,299 A | 3/1999 | Rastegar et al. | 600/232 |
| 6,042,541 A * | 3/2000 | Dobrovolny et al. | 600/228 |
| 6,315,260 B1 | 11/2001 | Lees | 248/286.1 |
| 6,622,980 B1 * | 9/2003 | Boucher et al. | 248/231.51 |

FOREIGN PATENT DOCUMENTS

| | | |
|---|---|---|
| FR | 1285135 | 5/1960 |
| WO | WO 03/028612 A1 | 9/2002 |

OTHER PUBLICATIONS

Thompson et al., Mechanical Aids at the Operating Table, *California Medicine*, vol. 97, No. 1., pp. 28-30, Jul. 1962.
Catalog, Great Eastern Lumber Company, Inc., Price List.
Catalog, Bookwalter Retractor.
Catalog, Pilling Retractor Systems, Narco Scientific, Mar. 1982.
Thompson, M.D., Catalog, Thompson Retractor, 1962.

* cited by examiner

STABILIZED TABLE RAIL CLAMP

The present application is based on and claims the benefit of U.S. provisional patent application Ser. No. 60/405,630, filed Aug. 23, 2002, the content of which is hereby incorporated by reference in its entirety.

BACKGROUND OF THE INVENTION

The present invention relates to a surgical retractor support apparatus. In particular, it relates to a clamping device that supports the surgical retractor support apparatus over an operating table.

Retractors are used during surgical procedures to retract the flesh at the edges of a surgical incision to expose a surgical site. The retractors are typically supported by a retractor support apparatus that is positioned over the operating table and about the surgical site. The retractor support apparatus is typically secured to a side rail attached to the side of the operating table by some type of clamping device.

In the past, two types of clamps have been used to position and attach a surgical retractor support apparatus to the side rail of an operating table. One type of clamp uses a mechanism in which a first member is pivotally attached to a second member and tightened in a jaw-like fashion around the side rail. The LeVahn, U.S. Pat. No. 4,355,631 and the LeVahn et al., U.S. Pat. No. 5,400,772, assigned to the same assignee as the present application, disclose clamping devices of this nature.

A second type of clamp supports a retractor support apparatus by employing a clamp member and a set screw. The set screw engages the side rail which secures the clamping member to the side rail. Examples of this type of rail clamp are disclosed in the Grieshaber, U.S. Pat. No. 3,040,739, and the Jascalevich, U.S. Pat. No. 3,710,783.

The prior art clamping mechanisms work well in situations when a lesser force is applied to the retractor support apparatus. However, when a large force is applied to the retractor support apparatus, the prior art clamps lack the stability to prevent the retractor support system from moving, tilting or leaning.

Another shortcoming of the prior art clamps is that the clamps are not always compatible to fit a variety of sizes of side rails. Therefore, an institution may be forced to own several different clamps to perform the same surgical procedure, depending on the design of the operating table.

BRIEF SUMMARY OF THE INVENTION

The present invention includes a clamping device which secures a retractor support apparatus to an opening table having a side rail. The clamping device includes a first clamping member disposed between a side of the operating table and the side rail. The clamping device also includes a second clamping member disposed between the side rail and the first clamping member. A first securing mechanism operably connects the first and second clamping members such that a force provided by the first securing mechanism causes the first and second clamping members to move in opposing directions and frictionally engage the side of the operating table and the side rail.

DETAILED DESCRIPTION

Figure 1:
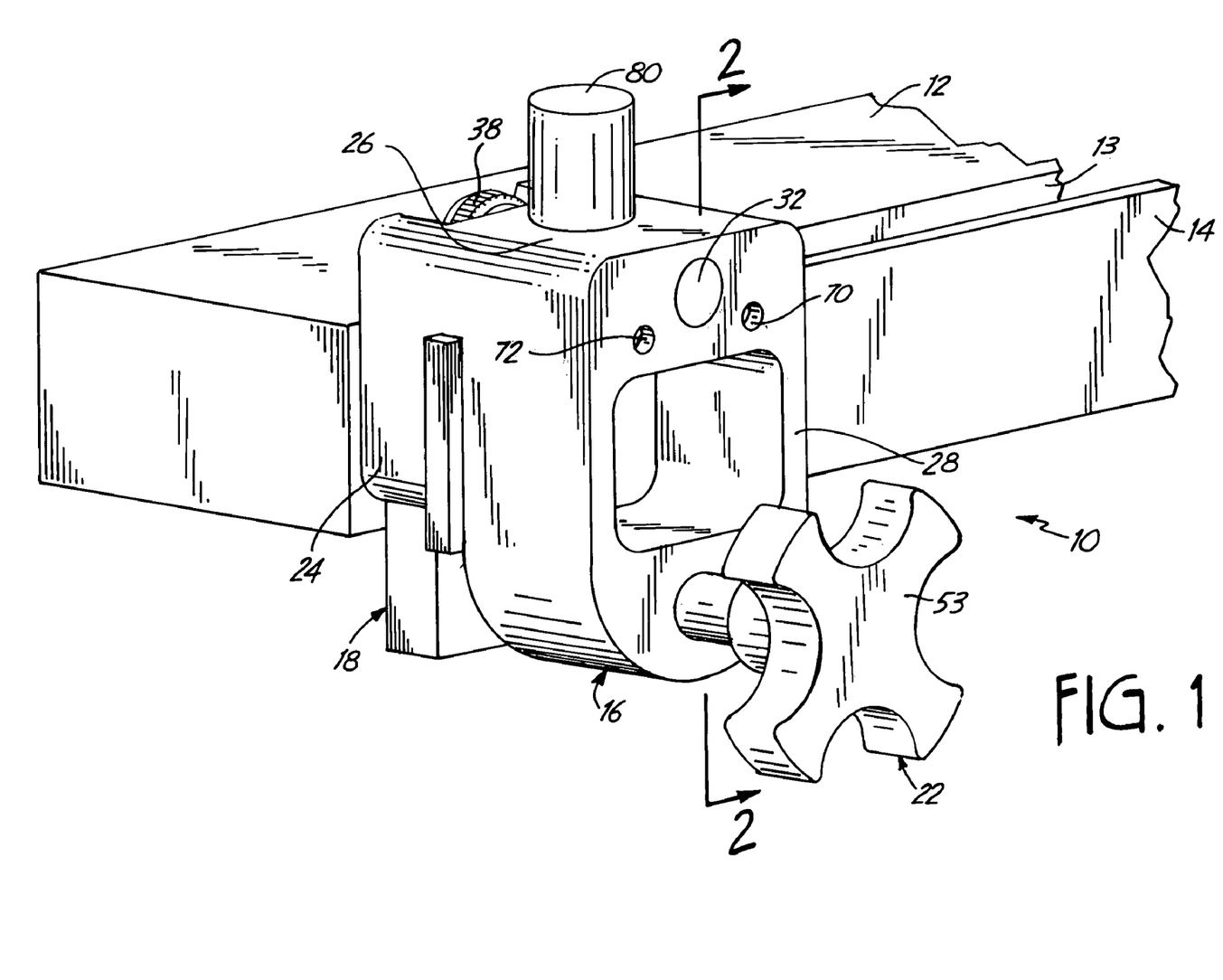
FIG. 1 is a perspective view of the first embodiment of the present invention.
Figure 2:
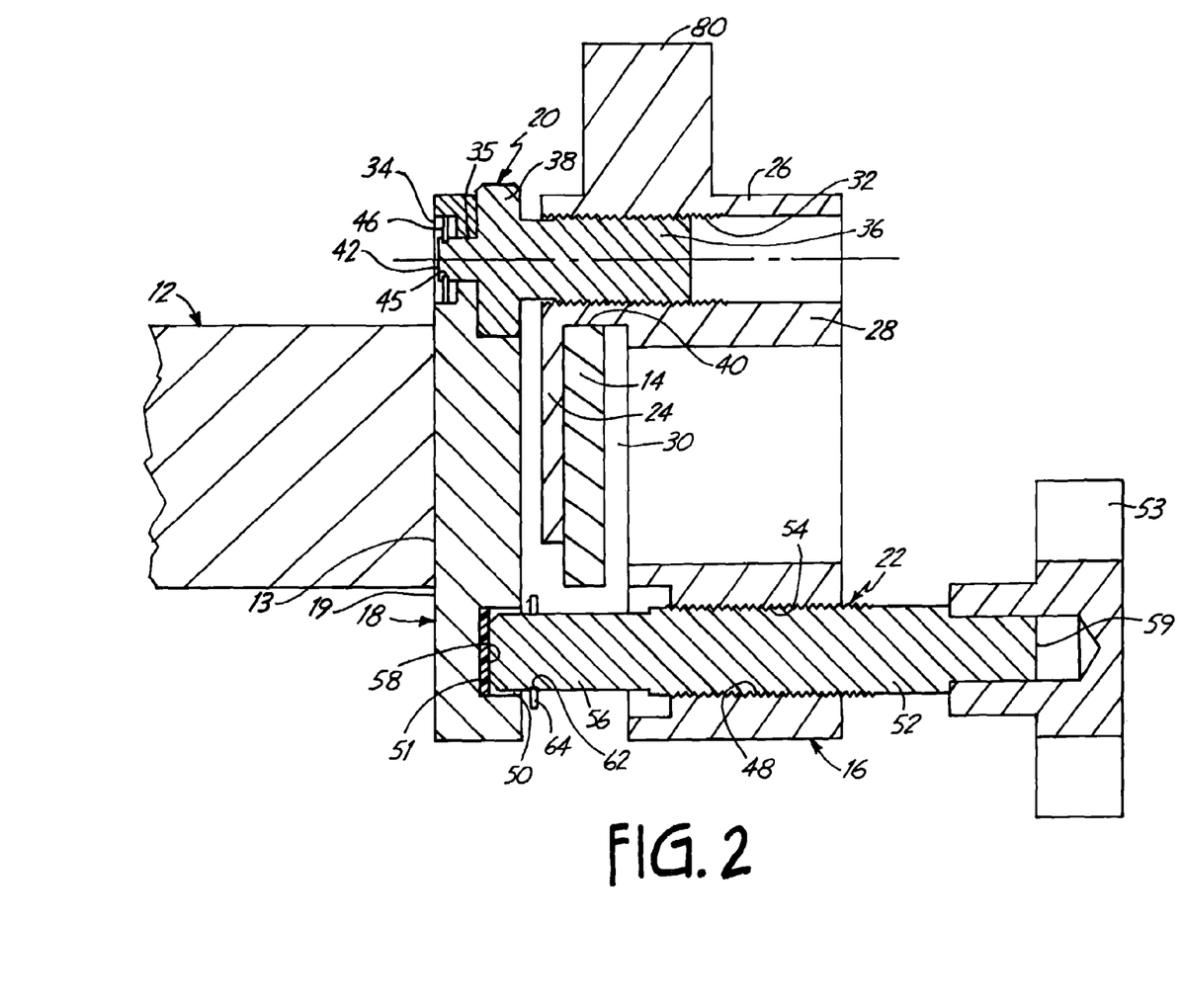
FIG. 2 is a sectional view of the first embodiment of the present invention along section line 2—2 of FIG. 1.
Figure 3:
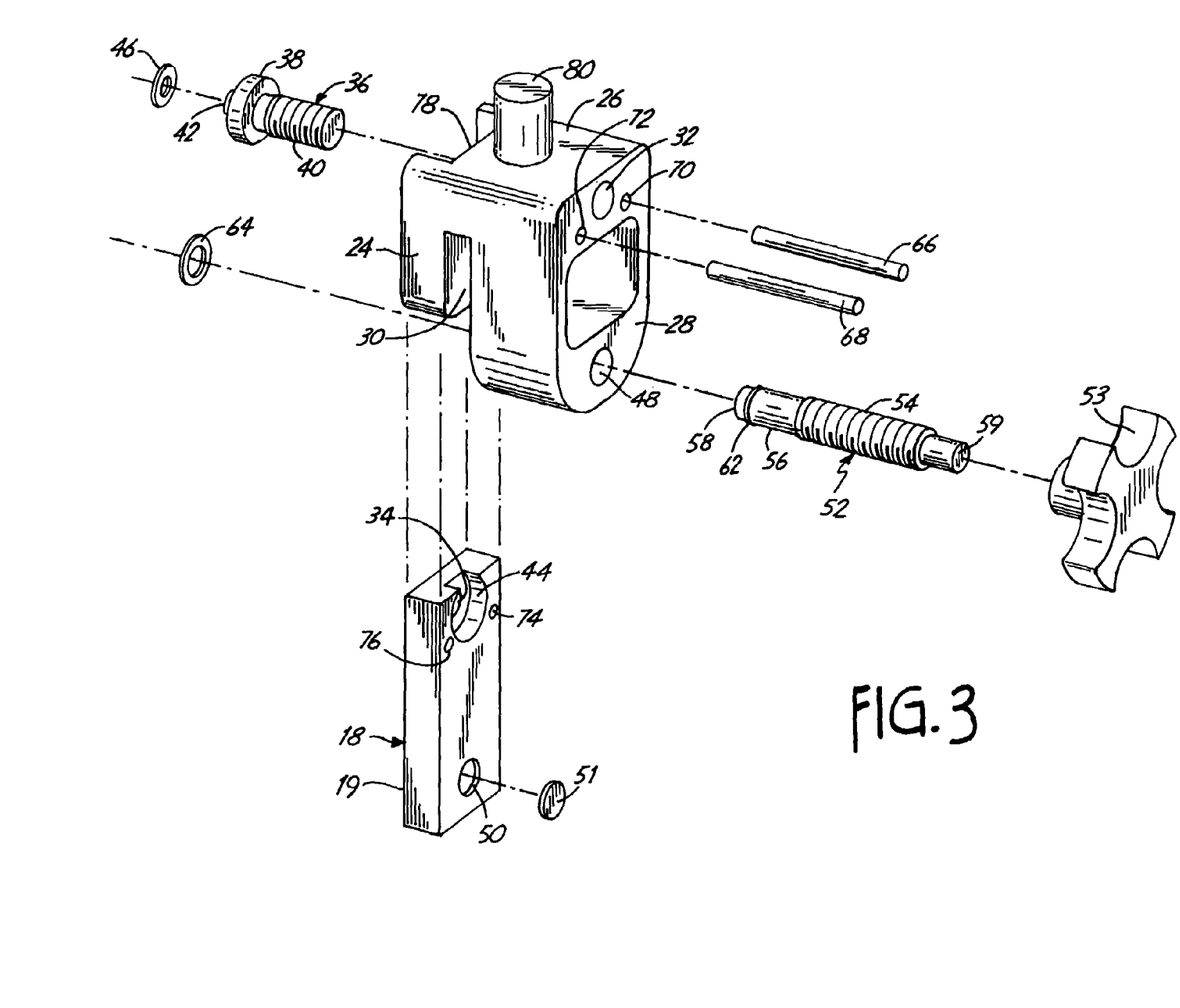
FIG. 3 is an exploded perspective view of the first embodiment of the present invention.

A table rail clamp of the present invention is generally illustrated in FIG. 1 at 10. A surgical table 12 typically includes a side rail 14 which is attached to a side 13 and along a length of the surgical table 12. The table rail clamp 10 includes a rail engaging portion 16 and a table engaging portion 18. Referring to FIGS. 2 and 3, first and second securing mechanisms 20, 22 apply forces to the rail engaging portion 16 and the table engaging portion 18 which move the rail engaging portion 16 and the table engaging portion 18 in opposing directions thereby frictionally securing the table rail clamp 10 between the side rail 14 and the side 13 of the surgical table 12.

Referring to FIGS. 1–3, the rail engaging portion 16 is designed to slidably engage the side rail 14 and is positionable along the length of the side rail 14. The rail engaging portion 16 includes a first clamp plate 24 which is disposed between the side of the surgical table 12 and the side rail 14. The rail engaging portion 16 also includes a top portion 26 which connects the first clamp plate 24 and a retaining portion 28. The retaining portion 28 is spaced apart from the first clamp plate 24 and positioned substantially parallel to the first clamp plate 24 such that the first clamp plate 24, the top portion 26 and the retaining portion 28 define a slot 30. Referring to FIG. 2, a width of the slot 30 is greater than a thickness of the side rail 14 allowing the rail engaging portion 16 to freely slide upon the side rail 14 when no force is applied to the rail engaging portion 16.

Referring to FIGS. 2 and 3, the table engaging portion 18 preferably is a second clamp plate which is disposed between the side 13 of the surgical table 14 and the first clamp plate 24. The table engaging portion 18 preferably includes a flat surface 19 which engages the side 13 of the table 12 which is also preferably flat. Although the preferred geometric configuration of the table engaging portion 18 is a plate, other geometric configurations are within the scope of the invention.

The table engaging portion 18 is operably attached to the rail engaging portion 16 by the first securing mechanism 20 and the second securing mechanism 22 as best illustrated in FIG. 2. The first securing mechanism 20 is positioned above a top surface of the rail 14 and preferably above a top edge of the side 13 of the surgical table 12. The second securing mechanism 22 is positioned below a bottom surface of the side rail 14 and preferably below a bottom edge of the side 13 of the surgical table 12.

The first securing mechanism 20 includes a first threaded bore 32 disposed within the rail engaging portion 16. The first threaded bore 32 within the rail engaging portion is aligned with a first bore 34 within the table engaging portion 18. A first threaded bolt 36 threadably engages the first threaded bore 32 and operably engages a shoulder 35 within the first bore 34 within the table engaging portion 18.

Referring to FIGS. 2 and 3, the first threaded bolt 36 includes an engaging ring 38. The engaging ring 38 is disposed proximate a threaded portion 40 of the first threaded bolt 36 and a selected distance from a first end 42 of the first threaded bolt 36. The table engaging portion 18 includes a cut out portion 44 about the first bore 34 which accommodates the engaging ring 38. The cut out portion 44 extends to a top end 23 of the table engaging portion 18 such that the engaging ring 38 is exposed and thereby allowing the first threaded bolt 36 to be rotated in a similar manner as a thumb screw. As the first threaded bolt 36 is rotated, the threaded engagement of the first threaded bolt 36 with the first threaded bore 32 creates a force which urges the rail engaging portion 16 and the table engaging portion 18 in opposing directions.

The first end 42 of the first threaded bolt 36 extends through the first bore 34 where the first threaded bolt 36 includes a groove 45 around a circumference thereof. A snap ring 46, having a larger diameter than an opening through the shoulder 35 within the first bore 34, is disposed within the groove 45 such that the second clamp plate 18 is operably attached to the first threaded bolt 36.

The second securing mechanism 22 also includes a second threaded bore 48 proximate a bottom end of the rail engaging portion 16 and a second bore 50 in the table engaging portion 18 aligned with the second threaded bore 48. A second threaded bolt 52 threadably engages the second threaded bore 48 and operably engages the second bore 50. A wear washer 51 is disposed within the second bore 50 to prevent galling of the table engaging portion 18. The second threaded bolt 52 has a threaded portion 54 proximate a middle of the bolt 52 and a smooth shaft 56 proximate a distal end 58. The distal end 58 of the second threaded bolt 52 extends into the second bore 50 and engages the table engaging portion 18 to provide an opposing force between the table engaging portion 18 and the rail engaging portion 16. A handle 53 is attached to a proximal end 59 of the second threaded bolt 52 to aid in manipulating the second threaded bolt 52.

The second threaded bolt 52 is retractable from the table engaging portion 18 to provide sufficient clearance to allow the clamp 10 to be lifted off of the side rail 14 and positioned on another operating table. A second snap ring 64 is disposed within a second groove 62 proximate the distal end 58 of the second threaded bolt 52. The second snap ring 64 has a larger diameter than the second threaded bore 48 and retains the second threaded bolt 52 within the second threaded bore 48 when threadable engagement between the second threaded bolt 52 and the second threaded bore 48 is disengaged.

Referring to FIG. 3, alignment pins 66, 68 are inserted through first and second alignment bores 70, 72 in the rail engaging portion 16 and first and second alignment bores 74, 76, the table engaging portion 18, respectively, to maintain the alignment of the rail engaging portion 16 and the table engaging portion 18. Additionally, a channel 78 within the rail engaging portion 16 cooperates with the table engaging portion 18 to maintain alignment of the rail engaging portion 16 and the table engaging portion 18.

In operation, the rail engaging portion 16 is positioned such that the side rail 14 is disposed within the slot 30 and the rail engaging portion 16 slidably engages the side rail 14. After positioning the rail engaging portion 16 about the side rail 14, the second threaded bolt 52 is manipulated to position the distal end 58 of the second threaded bolt 52 proximate the second bore 50.

With the second threaded bolt 52 aligned with the second bore 50 in the table engaging portion 18, the clamp 10 is slidably positioned on the side rail 14 to a selected position.

With the clamp 10 in the selected position, the first securing mechanism 20 is manipulated to force the table engaging portion 18 away from the rail engaging portion 16. In the preferred embodiment, a threaded bolt is used as the force providing mechanism 20 although one skilled in the art will recognize that a camming mechanism, eccentric, or irregularly shaped lobes are within the scope of the invention. The first threaded bolt 52 is manipulated until a top portion of the table engaging portion 18 is adjacent to the top edge of the side 13 of the surgical table 12.

With the top portion 26 of the table engaging portion 18 adjacent to the side 13 of the surgical table 12, the second threaded bolt 52 is manipulated to urge the bottom portion of the table engaging portion 18 proximate the bottom edge of the side 13 of the surgical table 12. With the top and bottom portions of the second clamp plate 18 adjacent to the side 13 of the surgical table 12, the first and second securing mechanism 20, 22 are further manipulated to displace the table engaging portion 18 away from the rail engaging portion 16 causing the rail engaging member 16 to move away from the side of the surgical table 12. The first and second securing mechanisms 20, 22 are manipulated until the first clamp plate 24 is adjacent to a side of the side rail 14.

Further manipulation of the first and second securing mechanisms 20, 22 creates an opposing force which frictionally engages the first clamp plate 24 with the side rail 14 and the table engaging portion 18 with the side 13 of the surgical table 12 thereby fixing the clamp 10 in a desired position. One skilled in the art will realize that having an even force along the height of the side rail 14 provides a more secure clamping mechanism than having a clamp engage only either the bottom or top of the side rail 14.

A support member 80 is attached to the top portion 26 of the rail engaging member 16, a portion of which is illustrated in FIGS. 1–3. The support member 80 extends upwardly thereby providing a support onto which other retractor supports (not shown) are clamped as described in U.S. Pat. Nos. 4,617,916; 4,718,151; 4,949,707 and 6,210,325.

Figure 4:
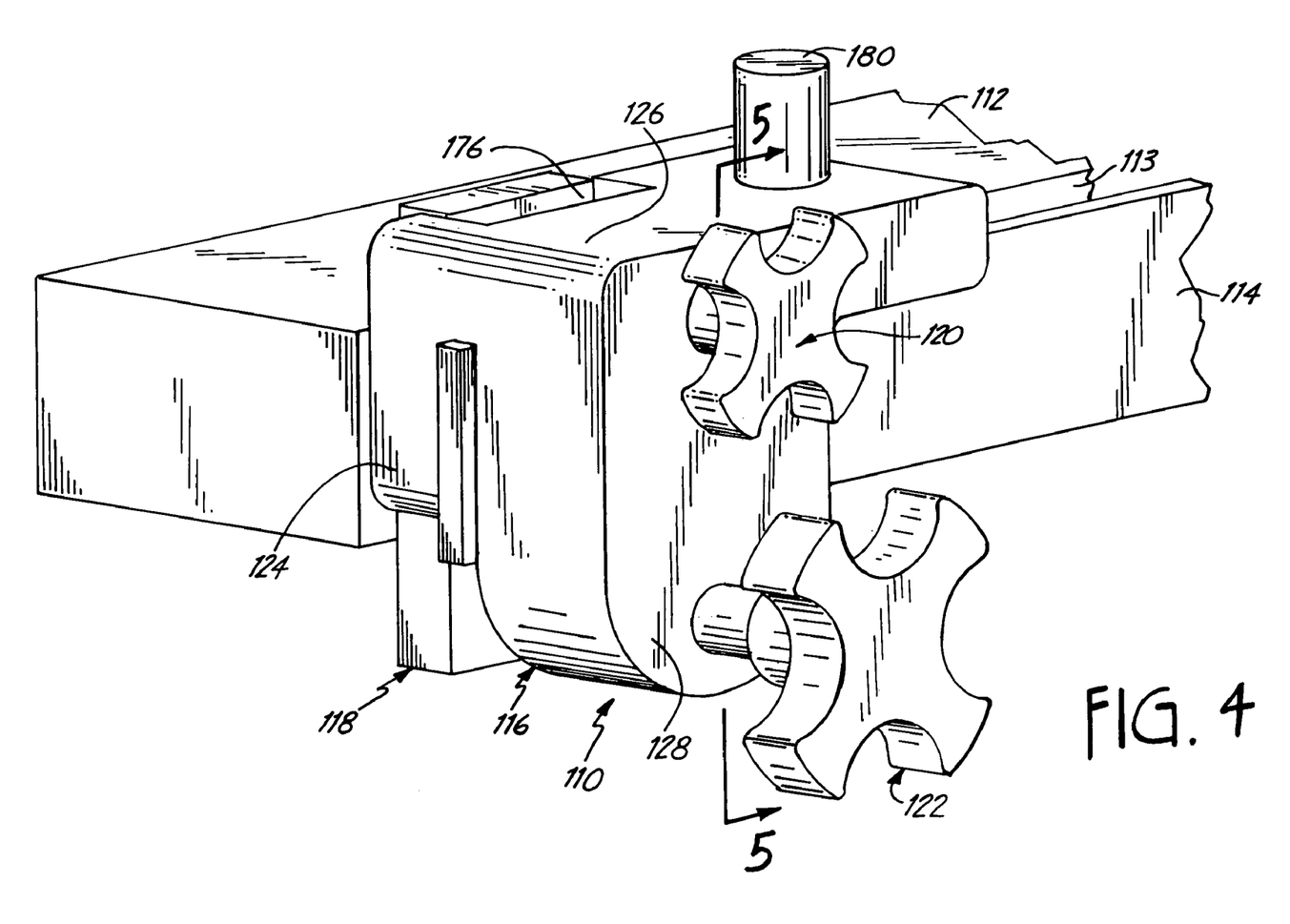
FIG. 4 is a perspective view of a second embodiment of the present invention.

An alternative embodiment of the table rail clamp of the present invention is generally illustrated in FIG. 4 at 110. The clamp 110 includes a rail engaging portion 116 and a table engaging portion 118. The first and second securing mechanisms 120, 122 apply forces to the rail engaging portion 116 and the table engaging portion 118 which move the rail engaging portion 116 and the table engaging portion 118 in opposing directions thereby frictionally securing the table rail clamp 110 between the side rail 114 and the side 113 of the surgical table 112 as best illustrated in FIG. 5.

Figure 5:
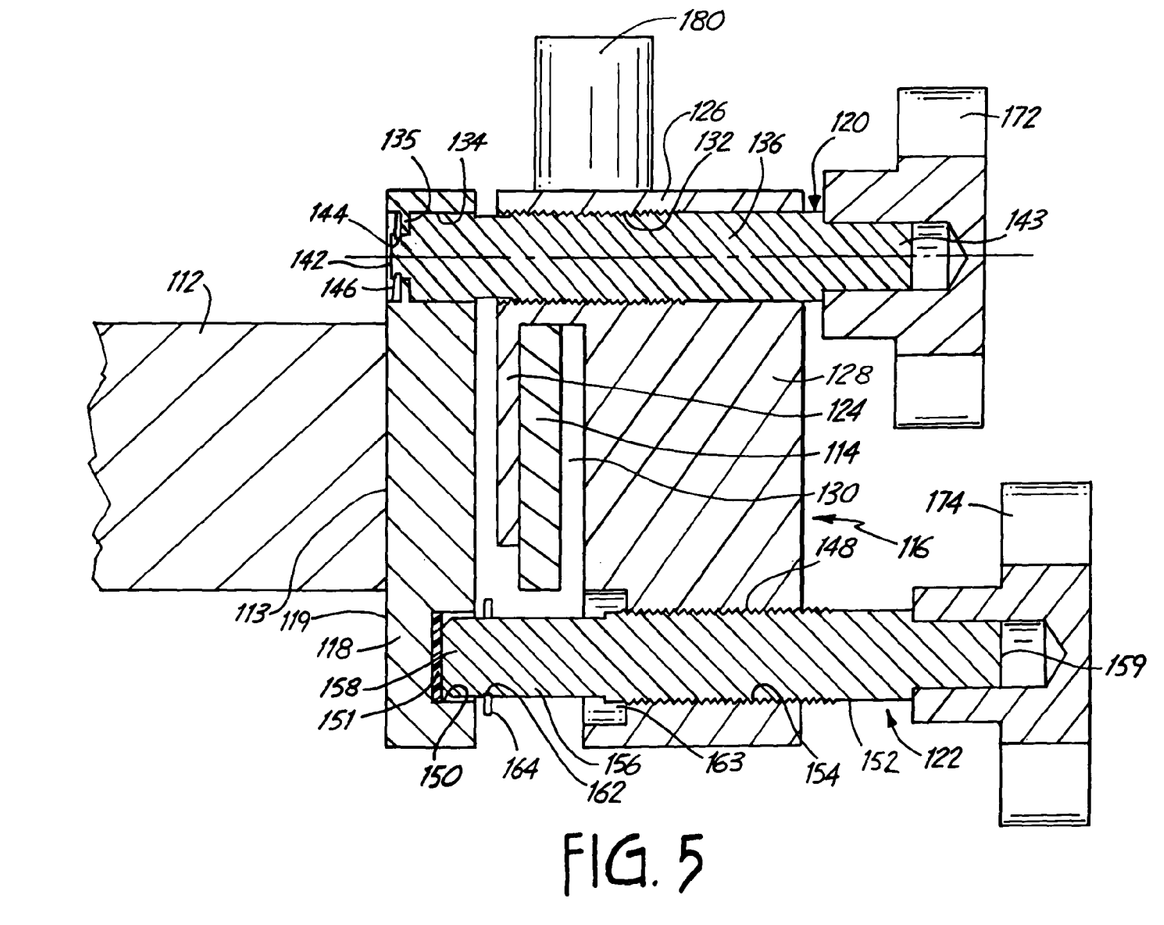
FIG. 5 is a sectional view of the second embodiment of the present invention along section line 5—5 of FIG. 4.
Figure 6:
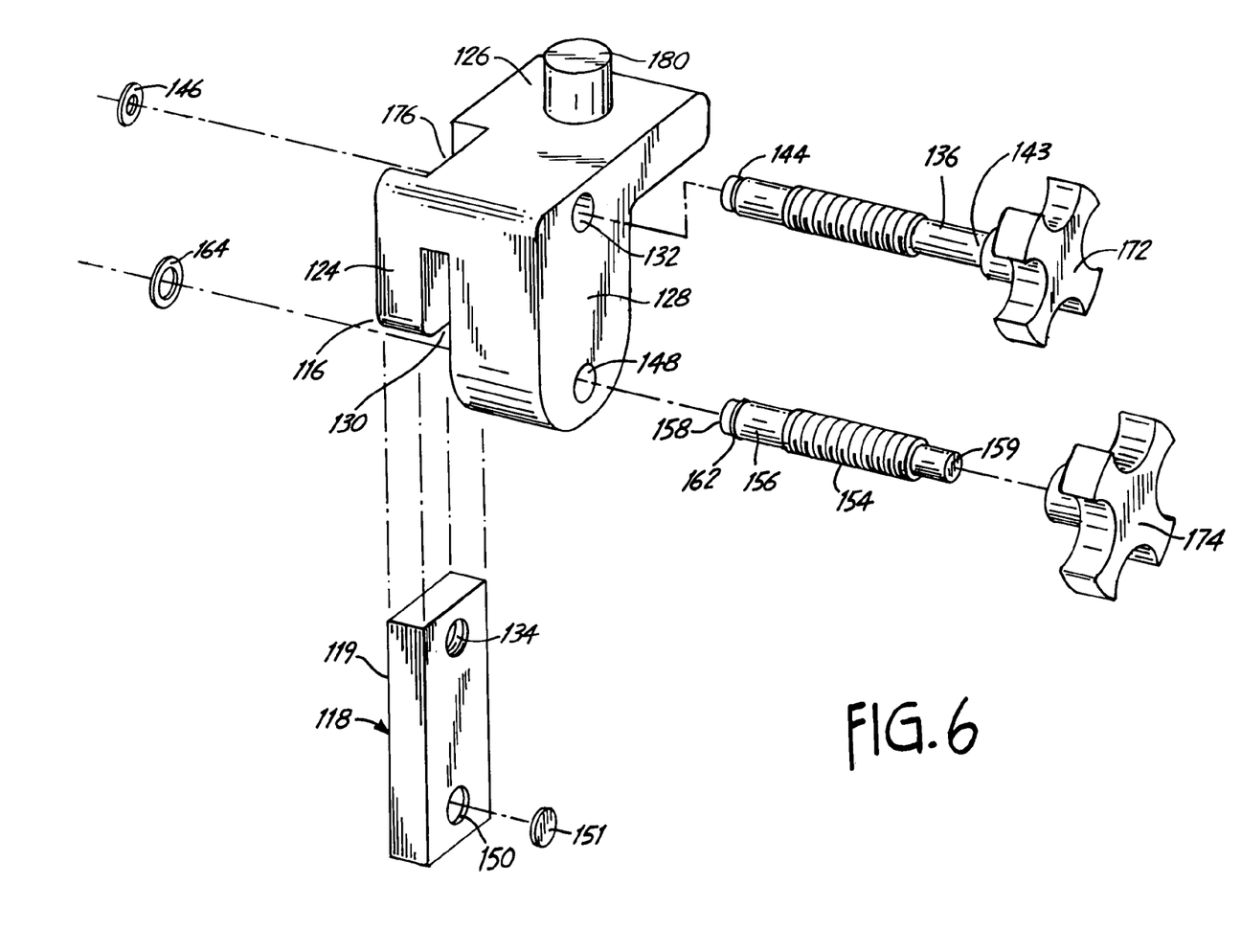
FIG. 6 is an exploded perspective view of the second embodiment of the present invention.

Referring to FIGS. 4–6, the rail engaging portion 116 is designed to slidably engage the side rail 114 and is positionable along the length of the side rail 114. The rail engaging portion 116 includes first clamp plate 124 which is disposed between the side 113 of the surgical table 112 and the side rail 114. The rail engaging portion 116 also includes a top portion 126 which connects the first clamp plate 124 and a retaining portion 128. The retaining portion 128 is spaced apart from the first clamp plate 124 and is positioned substantially parallel to the first clamp plate 124 such that the first clamp plate 124, the top portion 126 and the retaining portion 128 define a slot 130. A width of the slot 130 is greater than a thickness of the side rail 114 allowing the rail engaging portion 116 to freely slide upon the side rail 114 when no force is applied to the rail engaging portion 116.

The table engaging portion 118 preferably is a second clamp plate which is disposed between the side 113 of the surgical table 114 and the first clamp plate 124. The table engaging portion 118 preferably includes a flat surface 119 which engages the side 113 of the table 112 which is also preferably flat. Although the preferred geometric configuration of the table engaging portion 118 is a plate, other geometric configurations are within the scope of the invention.

The table engaging portion 118 is operably attached to the rail engaging portion 116 by the first securing mechanism 120 and the second securing mechanism 122. The first securing mechanism 120 is disposed above a top surface of the rail 114 and preferably above a top edge of the side 113 of the surgical table 112. The second securing mechanism 122 is disposed below a bottom surface of the side rail 114 and preferably below a bottom edge of the side 113 of the surgical table 112.

Referring to FIG. 5, the first securing mechanism 120 includes a first threaded bore 132 disposed within the rail engaging portion 116. A first bore 134 within the table engaging portion 118 is aligned with the first threaded bore 132 within the rail engaging portion 116. A first threaded bolt 136 threadably engages the threaded bore 132 and operably engages the first bore 134 within the table engaging portion 118.

A handle 172 is disposed at a second end 143 extending beyond the rail engaging portion 116 where the handle 172 allows the user of the clamp 110 to manipulate the threaded bolt 136. As the first threaded bolt 136 is rotated, the threaded engagement of the first threaded bolt 136 with the threaded bore 132 creates an opposing force which forces the rail engaging portion 116 and the table engaging portion 118 in opposing directions.

A groove 144 is disposed about a circumference of the first threaded bolt 136 proximate a first end 142 where the first end 142 extends through the first bore 134. A snap ring 146 with a diameter larger than an opening defined by a shoulder 135 within the first bore 134, is disposed within the groove 144 such that the table engaging portion 118 is operably attached to the first threaded bolt 136.

The second securing mechanism 122 also includes a second threaded bore 148 proximate a bottom end of the rail engaging portion 116 and a second bore 150 in the table engaging portion 118 aligned with the second threaded bore 148. A second threaded bolt 152 threadably engages the second threaded bore 148 and is disposed within the second bore 150 of the table engaging portion 118. A wear washer 151 is disposed within the second bore 150 to prevent galling of the table engaging portion 118. The second threaded bolt 152 has a threaded portion 154 proximate a middle of the bolt 152 and a smooth shaft 156 proximate a distal end 158. The distal end 158 of the second threaded bolt 152 cooperates with the second bore 150 to provide an opposing force between the table engaging portion 118 and the rail engaging portion 16. A handle 174 is disposed at a proximal end 159 of the second threaded bolt 152 to manipulate the position of the rail engaging portion 116 and the table engaging portion 116.

A second snap ring 164 is disposed within a second groove 162 proximate the distal end 158 of the second threaded bolt 152. The second snap ring 164 has a larger diameter than the second threaded bore 148 and retains the second threaded bolt 152 within the second threaded bore 148 when threadable engagement between the second threaded bolt 152 and the second threaded bore 148 is disengaged.

The second threaded bolt 152 is retractable from the table engaging portion 118 to provide the required clearance to allow the clamp 110 to be lifted off of the side rail 114 and positioned on another operating table. To provide the required clearance, the second snap ring 164 is retracted into a cavity 163 within the rail engaging portion 116. Additionally, a channel 176 within the rail engaging portion 116 cooperates with the table engaging portion 118 to maintain alignment of the rail engaging portion 116 and the table engaging portion 118.

In operation, the rail engaging portion 116 is positioned about the side rail 114 such that the side rail 114 is disposed within the slot 130 and the rail engaging portion 116 slidably engages the side rail 114. After disposing the rail engaging portion 116 about the side rail 114, the second threaded bolt 152 is manipulated to position the distal end 158 of the second threaded bolt 152 proximate the second bore 150.

With the second treaded bolt 152 aligned with the second bore 150 in the table engaging portion 118, the clamp 110 is slidably positioned on the side rail 114 to a selected position. With the clamp 110 in the selected position, the first securing mechanism 120 is manipulated to force the table engaging portion 118 away from the rail engaging portion 116. In the preferred embodiment, a threaded bolt is used as the force providing mechanism 120 although one skilled in the art will recognize that a camming mechanism, eccentric, or irregularly shaped lobes are within the scope of the invention. The first threaded bolt 152 is manipulated until a top portion of the table engaging portion 118 is adjacent to the top edge of the side 113 of the surgical table 112.

With the top portion 126 of the table engaging portion 118 adjacent to the side 113 of the surgical table 112, the second threaded bolt 152 is manipulated to urge the bottom portion of the table engaging portion 118 proximate the bottom edge of the side 113 of the surgical table 112. With the top and bottom portions of the second clamp plate 118 adjacent to the side 113 of the surgical table 112, the first and second securing mechanisms 120, 122 are further manipulated to displace the table engaging portion 118 away from the rail engaging portion 116 causing the rail engaging member 116 to move away from the side of the surgical table 112. The first and second securing mechanisms 120, 122 are manipulated until the first clamp plate 124 is adjacent to a side of the side rail 114.

Further manipulation of the first and second securing mechanisms 120, 122 creates an opposing force which frictionally engages the first clamp plate 124 with the surface of the side rail 114 and the table engaging portion 118 with the side 113 of the surgical table 112 thereby fixing the clamp 110 in a desired position as illustrated in FIG. 5. One skilled in the art will realize that having an even force along the height of the side rail 114 provides a more secure clamping mechanism than having a clamp engage only either the bottom or top of the side rail 114.

A support member 180 is attached to the top portion 126 of the rail engaging member 116, a portion of which is illustrated in FIGS. 4–6. The support member 180 extends upward thereby providing a support onto which other retractor supports (not shown) are clamped.

Although the present invention has been described with reference to preferred embodiments, workers skilled in the art will recognize that changes may be made in form and detail without departing from the spirit and scope of the invention.

What is claimed is:

1. A device for clamping a retractor support apparatus to an operating table, the operating table having a side rail, the device comprising:
    a first clamping member disposed between a side of the operating table and the side rail; and
    a second clamping member disposed between the side of the operating table and the first clamping member; and
    a mechanism operably connected to the first clamping member and the second clamping member such that the first and second clamping members are movable in opposing directions thereby frictionally engaging the first clamping member with the side rail and the second clamping member with the side of the operating table wherein the mechanism includes a first threaded rod engaging the first and second clamping members above the side rail and second threaded rod engaging the first and second clamping members below the side rail such that when the first and second threaded rods are turned, the clamping members move in the opposing directions and wherein the first and second rods threadably engage the first clamping member while freely rotating in engagement with the second clamping member.

2. The device of claim 1 and further including a U-shaped member positioned on the side rail with the first clamping member being one leg of the U-shaped member and the U-shaped member having a second leg being disposed on a side of the side rail opposite from the operating table and the first leg.

3. The device of claim 1 wherein the first and second threaded rods each have a handle fixedly attached thereto for turning the first and second threaded rods.

4. A clamping device for retaining a retractor support apparatus over an operating table, the operating table having a side rail, the clamping device comprising:
    a U-shaped member having first and second legs, the legs being disposed on opposite sides of the side rail;
    first and second rods threadably engaging the U-shaped member with the first threaded rod positioned above the side rail and the second threaded rod being positioned below the side rail, each of the rods having distal ends for acting against the operating table such that when the threaded rods are turned, the first and second legs are forced against the side rail, frictionally engaging the side rail and holding the U-shaped member in a clamped position against the side rail; and
    a clamping plate rotatably engaged by the distal ends of the first and second rods and positioned against the operating table to engage the operating table when at least one of the threaded rods is turned.

5. The clamping device of claim 4 and wherein both threaded rods are turned to force the first leg against the side rail.

6. A clamping device for retaining a retractor support apparatus over an operating table, the operating table having a side rail, the clamping device comprising:
    a first clamp plate disposed between the side rail and a side of the operating table;
    a second clamp plate disposed between the first clamp plate and the operating table wherein the second clamp plate engages the side of the operating table;
    a first force providing mechanism operably connected to the first clamp plate and the second clamp plate, the force providing mechanism providing a clamping force to the first clamp plate by interacting with the second clamp plate such that the first clamp plate is positioned in a first position wherein the first clamp plate frictionally engages the side rail, wherein the first force providing mechanism comprises:
        a first bore disposed in the second clamp plate;
        a first threaded bore disposed through the first clamp plate, wherein the first threaded bore is aligned with the first bore;
        a first threaded bolt threadably engaging the first threaded bore and operably engaging the first bore such that manipulation of the first threaded bolt positions the first clamp plate into either the first position where the first clamp plate frictionally engages the side rail or a second position wherein the first clamp plate does not frictionally engage the side rail;
        a top member attached to the first clamp plate; and
        a retaining member attached to the top member wherein the retaining member is spaced apart from the first clamp plate wherein the first clamp plate, the top member and the retaining member define a slot which slidably engages the side rail.

7. The device of claim 6 wherein the first threaded bolt further comprises an engaging surface, the engaging surface being manipulated to position the first clamp plate between the first position and the second position.

8. The device of claim 6 wherein the first threaded bolt further comprises a first handle attached to a distal end of the first threaded bolt wherein the first handle is manipulated to position the first clamp plate between the first position and the second position.

9. The device of claim 6 wherein the first force providing mechanism is disposed above a top end of the side rail and a top end of the side of the table.

10. The device of claim 6 and further comprising a second force providing mechanism operably connected to both the second clamp plate and the first clamp plate a distance from the first force providing mechanism, the second force providing mechanism providing a force to both the second clamp plate and the first clamp plate such that the first clamp plate frictionally engages the side rail.

11. The device of claim 10 wherein the second force providing mechanism comprises:
    a second bore disposed in the second clamp plate;
    a second threaded bore disposed through the first clamp plate, the second threaded bore aligned with the second bore; and
    a second threaded bolt threadably engaging the second threaded bore and wherein a proximal end of the second bolt operably engages the second bore such that manipulation of the second threaded bolt positions the first clamp plate into either a first position where the first clamp plate frictionally engages the side rail or a second position where the first clamp plate does not frictionally engage the side rail.

12. The device of claim 11 wherein the second threaded bolt further comprises a second handle attached to a distal end of the second threaded bolt wherein the second handle is manipulated to position the first clamp plate between the first position and the second position.

13. The device of claim 11 wherein the second force providing mechanism is disposed below a bottom end of the side rail.

14. A clamping device for retaining a retractor support apparatus over an operating table, the operating table having a side rail, the clamping device comprising:
    a first clamp plate disposed between the side rail and a side of the operating table;

a second clamp plate disposed between the first clamp plate and the operating table wherein the second clamp plate engages the side of the operating table;

a first force providing mechanism operably connected to the first clamp plate and the second clamp plate, the force providing mechanism providing a clamping force to the first clamp plate by interacting with the second clamp plate such that the first clamp plate is positioned in a first position wherein the first clamp plate frictionally engages the side rail; and a second force providing mechanism operably connected to both the second clamp plate and the first clamp plate a distance from the first force providing mechanism, the second force providing mechanism providing a force to both the second clamp plate and the first clamp plate such that the first clamp plate frictionally engages the side rail.

15. The device of claim 14 and further comprising:

a top member attached to the first clamp plate; and a retaining member attached to the top member wherein the retaining member is spaced apart from the first clamp plate wherein the first clamp plate, the top member and the retaining member define a slot which slidably engages the side rail.

16. The device of claim 14 wherein the first force providing mechanism comprises:

a first bore disposed into the second clamp plate;

a first threaded bore disposed through the first clamp plate, wherein the first threaded bore is aligned with the first bore; and a first threaded bolt threadably engaging the first threaded bore and operably engaging the first bore such that manipulation of the first threaded bolt positions the first clamp plate into either the first position where the first clamp plate frictionally engage the side rail or a second position wherein the first clamp plate does not frictionally engage the side rail.

17. The device of claim 16 wherein the first threaded bolt further comprises an engaging surface, the engaging surface being manipulated to position the first clamp plate between the first position and the second position.

18. The device of claim 16 wherein the first threaded bolt further comprises a first handle attached to a distal end of the first threaded bolt wherein the first handle is manipulated to position the first clamp plate between the first position and the second position.

19. The device of claim 16 wherein the first force providing mechanism is disposed above a top end of the side rail and a top end of the side of the table.

20. The device of claim 16 wherein the second force providing mechanism comprises:

a second bore disposed in the second clamp plate;

a second threaded bore disposed through the first clamp plate, the second threaded bore aligned with the second bore; and a second threaded bolt threadably engaging the second threaded bore and wherein a proximal end of the second bolt operably engages the second bore such that manipulation of the second threaded bolt positions the first clamp plate into either a first position where the first clamp plate frictionally engages the side rail or a second position where the first clamp plate does not frictionally engage the side rail.

21. The device of claim 20 wherein the second threaded bolt further comprises a second handle attached to a distal end of the second threaded bolt wherein the second handle is manipulated to position the first clamp plate between the first position and the second position.

22. The device of claim 20 wherein the second force providing mechanism is disposed below a bottom end of the side rail.

* * * * *